US005628961A

United States Patent [19]

Davis et al.

[11] Patent Number: 5,628,961
[45] Date of Patent: May 13, 1997

[54] APPARATUS FOR ASSAYING VISCOSITY CHANGES IN FLUID SAMPLES AND METHOD OF CONDUCTING SAME

[75] Inventors: Graham Davis, Plainsboro, N.J.; Imants R. Lauks, Rockcliff Park, Canada; Michael P. Zelin, Brooklyn, N.Y.

[73] Assignee: i-Stat Corporation, Princeton, N.J.

[21] Appl. No.: 413,836

[22] Filed: Mar. 30, 1995

Related U.S. Application Data

[62] Division of Ser. No. 142,130, Oct. 28, 1993, Pat. No. 5,447,440.

[51] Int. Cl.$^6$ .................................................. G01N 21/00
[52] U.S. Cl. ........................... 422/63; 422/73; 422/81; 422/82.02; 422/82.05; 435/286.5; 435/287.3; 435/288.7
[58] Field of Search .............................. 422/73, 63, 81, 422/82.02, 82.05; 436/66, 69; 23/54.04, 54.07, 64.41, 64.43; 435/286.5, 287.3, 288.7

[56] References Cited

U.S. PATENT DOCUMENTS

| 3,695,842 | 10/1972 | Mintz | 23/230 R |
|---|---|---|---|
| 4,756,884 | 7/1988 | Hillman et al. | 422/73 |
| 4,780,418 | 10/1988 | Kratzer | 436/69 |
| 4,948,961 | 8/1990 | Hillman et al. | 250/252.1 |
| 4,963,498 | 10/1990 | Hillman et al. | 436/69 |
| 5,004,923 | 4/1991 | Hillman et al. | 250/341 |
| 5,039,617 | 8/1991 | McDonald et al. | 436/69 |
| 5,086,002 | 2/1992 | Hillyard et al. | 436/69 |
| 5,096,669 | 3/1992 | Lauks et al. | 422/61 |
| 5,110,727 | 5/1992 | Oberhardt | 435/1.3 |
| 5,302,348 | 4/1994 | Cusack et al. | 422/73 |

FOREIGN PATENT DOCUMENTS

| 0395384 | 10/1990 | European Pat. Off. | G01N 33/48 |
|---|---|---|---|
| WO89/06803 | 7/1989 | WIPO | G01N 33/86 |

OTHER PUBLICATIONS

Haemostasis (1986) 16 (Suppl 5) pp. 71–72.
Laboratory Test Handbook, 2d Edition, David S. Jacobs, et al., "Coagulation", pp. 370–371.
Effective hemostatis in Cardiac Surgery, 1988, "Viscoelastic Measurement of Clot Formation: The Sonoclot", Salwa A. Shenaq, et al., pp. 183–193.
Proceedings of the American Academy of Cardiovascular Perfusion, vol. 9, Sep. 1988, Janene Keeth, et al., "A Clinical Evaluation of the Hemo Tec Act", pp. 22–25.
Clinical Chemistry, vol. 37, No. 4, 1991, Bruce J. Oberhardt, et al., "Dry Reagent Technology for Rapdi, Convenient Measurements of Blood Coagulation and Fribrinolysis", pp. 520–526.
J. Acoust. Sco. Am, vol. 90, No. 4, Pt. 1, Oct. 1991, J.C. Machado, et al., "An Ultrasonic Method To Measure Human Plasma Coagulation Time", pp. 1749–1753.

*Primary Examiner*—David A. Redding
*Attorney, Agent, or Firm*—Lowe, Price, LeBlanc & Becker

[57] ABSTRACT

The present invention relates to an apparatus for conducting a variety of assays that are responsive to a change in the viscosity of a sample fluid and relates to methods of conducting such assays. In particular, the present invention is related to the use of a cartridge for conducting one or more coagulation assays or, conversely, fibrinolysis assays. The disclosed device enjoys simplicity and is adaptable to the point-of-care clinical diagnostic area, including use in accident sites, emergency rooms, surgery or intensive care units.

70 Claims, 11 Drawing Sheets

DIAPHRAGM OSCILLATION

APPARATUS FOR ASSAYING VISCOSITY CHANGES IN FLUID SAMPLES AND METHOD OF CONDUCTING SAME

This is a division of application Ser. No. 08/142,130, filed on Oct. 28, 1993, now U.S. Pat. No. 5,447,440.

FIELD OF THE INVENTION

The present invention relates to an apparatus for conducting a variety of assays that are responsive to a change in the viscosity of a sample fluid and relates to methods of conducting such assays. In particular, the present invention is related to the use of a cartridge for conducting one or more coagulation assays or, conversely, fibrinolysis assays. The present invention makes adventitious use of a pump means for moving a fluid sample. In one embodiment, sample movement is achieved by reversibly, rapidly, and reproducibly applying pressure to a sample fluid to produce a substantially reciprocating motion that is, in turn, detectable by an appropriate sensor. The disclosed device enjoys simplicity and is adaptable to the point-of-care clinical diagnostic area, including use in accident sites, emergency rooms or medical intensive care units.

BACKGROUND OF THE INVENTION

Keeping blood in a fluid state, termed hemostasis, requires a subtle balance of pro- and anticoagulants. Procoagulants prevent excessive bleeding by blocking blood flow from a damaged vessel, whereas anticoagulants prevent clots from forming in the circulating system which could otherwise block blood vessels and lead to myocardial infarction or stroke.

The biochemical sequence leading to a blood clot is termed the coagulation cascade. The mechanism is based on catalytic conversion of fibrinogen, a soluble plasma protein, to insoluble fibrin. The enzyme catalyzing this reaction is thrombin, which does not permanently circulate in the blood in an active form but exists as prothrombin, the inactive precursor of thrombin. Conversion to thrombin occurs in the presence of calcium ions and tissue thromboplastin. This mechanism is known as the extrinsic pathway. A second, more complex, intrinsic pathway is activated by clotting factors associated with platelets and is well understood in the art.

Breakdown of a blood clot, termed fibrinolysis, requires the conversion of fibrin to a soluble product. This lysis is catalyzed by the proteolytic enzyme plasmin, which circulates in an inactive form, plasminogen. Tissue plasminogen activator (tPA), bacterial hemolytic enzymes (e.g., streptokinase), and proteolytic human enzymes found in urine (e.g., urokinase) all activate plasminogen. These materials are used in thrombolytic therapy.

Diagnosis of hemorrhagic conditions such as hemophilia, where one or more of the twelve blood clotting factors may be defective, can be achieved by a wide variety of coagulation tests. In addition, several tests have been developed to monitor the progress of thrombolytic therapy. Other tests have been developed to signal a prethrombolytic or hypercoagulable state, or monitor the effect of administering protamine to patients during cardiopulmonary bypass surgery. However, the main value of coagulation tests is in monitoring oral and intravenous anticoagulation therapy. Two of the key diagnostic tests are activated partial thromboplastin time (APTT) and prothrombin time (PT).

An APTT test evaluates the intrinsic and common pathways of coagulation. For this reason APTT is often used to monitor intravenous heparin anticoagulation therapy. Specifically, it measures the time for a fibrin clot to form after the activating agent, calcium, and a phospholipid have been added to the citrated blood sample. Heparin administration has the effect of suppressing clot formation.

A PT test evaluates the extrinsic and common pathways of coagulation and, therefore, is used to monitor oral anticoagulation therapy. The oral anticoagulant coumadin suppresses the formation of prothrombin. Consequently, the test is based on the addition of calcium and tissue thromboplastin to the blood sample.

The standard laboratory technology for coagulation tests typically uses a turbidimetric method (See, for example, U.S. Pat. No. 4,497,774). For analysis, whole-blood samples are collected into a citrate vacutainer and then centrifuged. The assay is performed with plasma to which a sufficient excess of calcium has been added to neutralize the effect of citrate. For a PT test, tissue thromboplastin is provided as a dry reagent that is reconstituted before use. This reagent is thermally sensitive and is maintained at 4 degrees C by the instruments. Aliquots of sample and reagent are transferred to a cuvette heated at 37 degrees C, and the measurement is made based on a change in optical density.

As an alternative to the turbidimetric method, Beker et al. (See, *Haemostasis* (1982) 12:73) introduced a chromogenic PT reagent (Thromboquant PT). The assay is based on the hydrolysis of p-nitroaniline from a modified peptide, Tos-Gly-Pro-Arg-pNA, by thrombin and is monitored spectrophotometrically.

Coagulation monitors are known for the analysis of whole blood. For example, a unit-use cartridge has been described in which dry reagents are placed into the analyzer which is then heated to 37 degrees C before a drop of blood is introduced. The sample is mixed with the reagent by capillary draw. The detection mechanism is based on laser light passing through the sample. Blood cells moving along the flow path yield a speckled pattern specific to unclotted blood. When the blood clots, movement ceases producing a pattern specific to clotted blood. Several patents disclose aspects of this technology and are described further, below.

U.S. Pat. No. 4,731,330 discloses a lyophilized whole-blood control sample consisting of fixed red blood cells and plasma solids including coagulation factors. Standard plasma controls cannot be used with this system because detection is based on the motion of red blood cells. U.S. Pat. No. 4,756,884 discloses the component parts of the cartridge technology, which is based on capillary draw, including certain antibodies and reagents for blood clotting. U.S. Pat. No. 4,948,961 discloses the components and method of use of an optical simulator cartridge used with the above instrument. U.S. Pat. No. 4,952,373 discloses a plastic safety shield that prevents blood from being inadvertently transferred from the blood entry port of the cartridge into testing region of the instrument.

U.S. Pat. No. 4,963,498 discloses a method of obtaining chemical information from the capillary draw cartridge. U.S. Pat. No. 5,004,923 discloses optical features by which the above instrument interrogates the cartridge. U.S. Pat. No. 5,039,617 discloses a device for APTT using whole-blood in which the sample is mixed with reagents as it is drawn by capillary action along a fluid path. The activating reagent, sulfatide or sulfoglycosylsphingolipid, provides a clot formation that is independent of hematocrit. EP 0368624 A2 discloses a method for providing dry, yet easily resuspendible, stable latex particles on a surface. EP 0395384 A2 discloses a coding method by which different types of cartridges can be identified.

A unit-use cartridge has also been described which comprises two capillary tubes that simultaneously draw blood from a single finger-stick. The design allows for duplicate measurement or two different measurements based on different reagent coatings. The PCT application WO 89/06803 describes the above apparatus for measuring blood coagulation based on changes in light permeability through a capillary tube.

On the other hand, U.S. Pat. No. 3,695,842 describes a method of analyzing the transformation of a liquid to a gelatinous or solid mass and is applied to PT and APTT. The coagulation system uses a vacutainer that contains all the necessary reagents, as well as a ferromagnetic component. Once the blood sample has been drawn into the vacutainer, it is placed into the instrument in an inclined manner. This procedure makes the ferromagnetic component sit at the bottom of the tube in close proximity to a magnetic reed switch. As the sample is rotated, gravity ensures that the component remains close to the reed switch. However, as the blood starts to clot, viscosity increases to the point where the component starts to rotate with the blood sample. The reed switch is thus activated, enabling a coagulation time to be estimated.

Yet another format has been described based on the use of magnetic particles mixed into a dry reagent contained within a flat capillary chamber. An applied oscillating magnetic field from the instrument causes the particles to oscillate once the reagent has dissolved in the blood. This motion is monitored optically. When the blood clots, the particles become entrapped and motion is diminished. Fibrinolysis assays are performed by monitoring the reverse process (See, Oberhardt et al., *Clin, Chem.* (1992) 37:520). The above magnetic particle-based method is also described in U.S. Pat. No. 5,110,727.

Another method of detecting coagulation is based on ultrasound scattering from 200 micron glass spheres suspended in a blood sample. Amplitude and phase changes of the scattered waves are used to detect coagulation (See, Machado et al., *J. Acoust. Soc. Am.* (1991) 90:1749).

Shenaq and Saleem, in "Effective Hemostasis in Cardiac Surgery," Eds: Ellison, N. and Jobes, D. R., Saunder & Co., (1988), utilize a sonic probe that is inserted into a cuvette containing the sample and reagents. The sonic probe responds to clot formation in the cuvette and, thus, can be used to measure the coagulation time.

An automatic coagulation timer has been described which measures the activated clotting time (ACT) in blood samples from patients during cardiopulmonary bypass. The sample is added to a cartridge which incorporates a stirring device on to which the clot forms. Motion of the stirring device is controlled by a photo optical detector (See, Keeth et al., *Proceedings Am. Acad. Cardiovascular Perfusion* (1988) 9:22).

An instrument for automatically recording clot lysis time based on a change in electrical conductivity has been reported (See, Wilkens and Back, *Am. J. Clin. Pathol.* (1976) 66:124). In the first step, streptokinase, thrombin and fibrinogen are added to a tube. Once a clot is formed the tube is partially inverted so that as streptokinase dissolves the clot, solution drains down the tube and drips into a second tube that has one electrode positioned at the bottom and another further up the tube. When the fluid reaches the second electrode a digital timer is stopped yielding an estimate of the clot dissolution time.

Another method of measuring clot lysis time based on breaking an electrical circuit maintained by a single fibrin strand has been reported (See, Folus and Kramer, *J. Clin. Pathol.* (1976) 54:361).

The disclosure of U.S. Pat. No. 5,096,669 includes the general format for blood chemistry testing (e.g., potassium and glucose blood levels) and the use of a bladder to move a sample fluid to a sensor region in a single direction. In particular, variation of the speed or direction of motion or the oscillation of a fluid sample is nowhere disclosed, taught or suggested.

Therefore, there remains a need for an apparatus and method of conducting assays that are responsive to changes in the viscosity of a fluid sample, which apparatus and method can be used at the point of care, especially locations, such as a doctor's office, which have no immediate access to a centralized testing facility, and which apparatus and method can be optionally produced by microfabrication methods and be readily adapted to include a multiplicity of tests, including blood gas and analyte testing.

SUMMARY OF THE INVENTION

It has now been surprisingly discovered that the needs enumerated above, and more, can be fulfilled by the apparatus and method of the present invention. In a preferred embodiment of the invention, a disposable, single-use cartridge is disclosed which, along with an external reading device, is capable of providing information relating to the propensity of a fluid sample to undergo changes in viscosity. In particular, diagnostic data on biological fluids, can be obtained such as clotting and fibrinolysis characteristics of whole blood samples.

Most importantly, the apparatus and method disclosed can include a battery of tests, all of which can be conducted simultaneously on a single fluid sample, usually in a matter of tens of seconds. For example, the time required to perform a normal PT test is about 12 seconds, while about 300–500 seconds may be needed for ACT tests using the blood from highly heparinized patients. The apparatus and method of the present invention is preferably adapted to make use of microfabrication methods and devices, especially microfabricated electrochemical sensors, to allow optimum cartridge configuration and reproducible data acquisition, handling, processing, and storage.

Thus, in its most general sense, the present invention relates to a cartridge for measuring a change in the viscosity of a fluid sample comprising: (a) a housing capable of being charged with a fluid sample and equipped with a sample displacement means for applying a force against the fluid sample effective to displace at least a portion of the fluid sample within the housing; (b) at least one reagent, contained within the housing, capable after contact with the fluid sample of promoting a change in the viscosity of the fluid sample; (c) at least one sensing means, contained within the housing, capable of detecting the displacement of the fluid sample.

In particular embodiments of the present invention the housing is equipped with one or more connecting means for engaging the housing with one or more mechanical, electronic or optical devices. For example, the cartridge may have electromechanical connectors to allow the cartridge to be engaged to an external reading device that performs a variety of functions including, but not limited to, recording, displaying, manipulating, storing or, otherwise, utilizing the measurements that can be carried out using the cartridge of the invention.

Another device to which the invention may be connected is an optical detection means that allows the determination of the position of a gas/liquid interface. Yet another can be a device that comprises a sample retaining means capable of charging the housing with the fluid sample. In preferred embodiments, the sample retaining means is also a fluid sampling means that, for example, can be used to draw a sample. The sample retaining/sampling means can then be connected to the cartridge of the present invention to charge the housing with the fluid sample. In other embodiments of the invention, the sample retaining means simply forms an integral part of the housing and can be loaded with the fluid sample.

In the present invention, the cartridge is equipped with a means for displacement of the fluid sample. For instance, the cartridge may be connected to an external pump means capable of then exerting a force against the fluid sample to move the sample within the housing. Alternatively, the sample displacement means may be a pump means that already forms an integral part of the cartridge. In any event, actuation of the sample displacement means allows at least a portion of the fluid sample to move across the sensing means.

In a preferred embodiment of the invention the force that is applied to the fluid sample, as well as its subsequent movement, is reversible so that at least a portion of the fluid sample is displaced back and forth across the sensing means in a substantially reciprocating manner. On contact of the fluid sample with the reagent, the subsequent changes in the viscosity of the fluid sample are then detected, in turn, by monitoring the fluid sample oscillation frequency, amplitude or changes therein. Alternatively, the sensing means is capable of detecting changes in the electrical properties of the fluid sample itself. In yet another embodiment of the invention, the sensing means can detect the position of the interface between a gas and a liquid (e.g., the gas/liquid interface between air and the fluid sample or between air and calibrant).

In a specific embodiment of the present invention, an apparatus is disclosed for conducting an assay that is responsive to a change in the viscosity of a fluid sample comprising: (a) at least one sensor sensitive to the displacement of a fluid sample across the sensor; (b) at least one reagent capable of promoting a change in the viscosity of a fluid sample; (c) a sample retainer for retaining a fluid sample out of contact with the sensor and the reagent; and (d) pump means for applying pressure against a fluid sample in the sample retainer to displace at least a portion of the fluid sample across the sensor. Preferably, the force or pressure is applied reversibly to cause the fluid sample to move in a substantially reciprocating manner, such that the fluid sample contacts the reagent that promotes the change in the viscosity of the fluid sample. In particular embodiments of the present invention, a pump means is provided which comprises a resilient diaphragm in fluid communication with the sample retainer. A preferred diaphragm may be equipped with an internal spring or an internal rubber sponge to promote the rapid, reproducible compression and decompression of the diaphragm.

As mentioned previously, the present invention also provides cartridges and methods of their use in which the cartridges may be coupled to an external reading device that performs a number of functions. Hence, the present invention also relates to an apparatus in which the sensor provides a signal to an external reading device that actuates a plunger for compressing and decompressing the diaphragm. Where the sensor is a conductivity sensor, preferably a microfabricated conductivity sensor, the signal is a conductivity output. In one embodiment, output signals below a first preselected value cause the reading device to actuate the plunger to compress the diaphragm, and output signals above a second preselected value cause the reading device to actuate the plunger to decompress the diaphragm. In addition to providing a feedback methodology, the external reading device may also provide signal processing capability in which raw data may be processed to enhance the amount of useful information that may be obtained from a given assay. Alternatively, the diaphragm can be compressed and decompressed at a constant preselected rate and the response of the fluid sample undergoing the change in viscosity is monitored by the sensor. Other aspects of the present invention include, cartridges that may be maintained at a given temperature, preferably at physiological temperature.

Various fluid samples may be assayed according to the present invention, including, but not limited to, biological fluids, such as whole blood and plasma. The present invention is also particularly useful for conducting assays on anticoagulated blood samples, including, but not limited to, heparinized or citrated whole blood.

It is, therefore, an object of the present invention to provide an apparatus for conducting a blood test for prothrombin time comprising: (a) at least one conductivity sensor sensitive to the displacement of a blood sample across the sensor; (b) at least one reagent mixture comprising thromboplastin and calcium ions; (c) a sample retainer for retaining the blood sample out of contact with the sensor and the reagent; (d) pump means for reversibly applying pressure against the blood sample in the sample retainer to displace at least a portion of the blood sample across the sensor, preferably, in a substantially reciprocating manner, the reagent contacting and promoting the coagulation of the blood sample.

It is another object of the present invention to provide an apparatus for conducting a blood test for activated partial thromboplastin time comprising: (a) at least one conductivity sensor sensitive to the displacement of a blood sample across the sensor; (b) at least one reagent mixture comprising a phospholipid and calcium ions; (c) a sample retainer for retaining the blood sample out of contact with the sensor and the reagent; (d) pump means for reversibly applying pressure against the blood sample in the sample retainer to displace at least a portion of the blood sample across the sensor, preferably, in a substantially reciprocating manner, the reagent contacting and promoting the coagulation of the blood sample.

Yet another object of the present invention relates to the disclosure of an apparatus for conducting a blood fibrinolysis test comprising: (a) at least one sensor sensitive to the displacement of a blood sample across the sensor; (b) at least one reagent capable of promoting the coagulation or partial coagulation of the blood sample; (c) a sample retainer for retaining the blood sample out of contact with the sensor and the reagent; (d) pump means for reversibly applying pressure against the blood sample in the sample retainer to displace at least a portion of the blood sample across the sensor, preferably, in a substantially reciprocating manner, the reagent contacting the whole blood to provide coagulated or partially coagulated blood, the pump means further capable of maintaining the reversibly applied pressure against the coagulated or partially coagulated whole blood until fibrinolytic processes cause the coagulated or partially coagulated whole blood to become less viscous, allowing increased or greater displacement of at least a portion of the lysed blood sample across the sensor, preferably, in a substantially reciprocating manner.

The cartridges of the present invention may further comprise a calibrant fluid at least a portion of which may be displaced across the sensor for the purpose of calibrating the sensor. It is, thus, contemplated that the calibrant fluid may be displaced across the sensor, preferably, in a substantially reciprocating manner while the calibrant fluid is in fluid communication with the blood or fluid sample, such that the blood or fluid sample need not be in direct contact with the sensor for the sensor to detect the change in the viscosity of the blood or fluid sample.

A further object of the present invention is the disclosure of a method of conducting an assay responsive to a change in the viscosity of a fluid sample comprising: (a) placing a fluid sample in a sample retainer for retaining the fluid sample out of contact with a sensor and a reagent, the sensor sensitive to the displacement of the fluid sample across the sensor and the reagent capable of promoting a change in the viscosity of the fluid sample; (b) applying pressure against the fluid sample in the sample retainer to displace at least a portion of the fluid sample across the sensor. Preferably, the force or pressure is applied reversibly such that the fluid sample moves in a substantially reciprocating manner, such that the fluid sample contacts the reagent that promotes the viscosity change of the fluid sample; (c) detecting the displacement of the fluid sample across the sensor to indicate a change in the viscosity of the fluid sample.

Yet a further object of the present invention is a method of conducting a blood fibrinolysis test, as described herein. The fibrinolysis test method of the present invention may further comprise treating the sample with a second reagent capable of promoting the fibrinolysis of the sample when the sample is coagulated or partially coagulated. Such fibrinolysis promoting agent may include, without being limited to, tissue plasminogen activator (tPA), streptokinase and urokinase.

A method of selecting a fibrinolysis promoting agent useful in the treatment of a subject is also disclosed, which method comprises: (a) conducting a fibrinolysis test on a sample of blood obtained from a subject, the test comprising, (i) placing the sample in a sample retainer for retaining the sample out of contact with a sensor and a reagent, the sensor sensitive to the displacement of the sample across the sensor and the reagent capable of promoting the coagulation of the sample, (ii) reversibly applying pressure against the sample in the sample retainer to displace at least a portion of the sample across the sensor, preferably, in a substantially reciprocating manner, such that the sample contacts the reagent that promotes the coagulation or partial coagulation of the sample, (iii) treating the sample at any time before or after the sample contacts the reagent with a fibrinolysis promoting agent, and (iv) maintaining the reversibly applied pressure against the coagulated or partially coagulated sample until fibrinolytic processes cause the coagulated or partially coagulated sample to become less viscous, allowing increased displacement of at least a portion of the lysed sample across the sensor, preferably, in a substantially reciprocating manner;

(b) interpreting the test results to determine an efficacious fibrinolysis promoting agent for the subject.

In the immediately foregoing test, more than one fibrinolysis test using one or more types of fibrinolysis promoting agents can be conducted in one cartridge. Preferably, multiple conduits, each holding a different promoter, are connected to the sample retainer. Of course, duplicate runs of the same promoter or reagent can be conducted on a single cartridge having multiple conduits. Alternatively, the results of multiple "single" tests are compared to determine an effective, or if desired, the most effective fibrinolysis promoter for the particular subject.

The present invention further encompasses a disposable, single-use cartridge comprised of a plurality of microfabricated sensors for the determination of the presence or concentration of one or more analytes in a sample fluid, along with a microfabricated sensor for the determination of changes in the viscosity of the sample fluid.

Other objects of the present invention will be evident to those of ordinary skill, particularly upon consideration of the following detailed description of the preferred embodiments.

DETAILED DESCRIPTION OF THE PREFERRED EMBODIMENTS

The present invention relates to an apparatus, preferably in the form of a cartridge, which can be used for conducting a variety of assays responsive to the change in the viscosity of a fluid sample, including assays involving whole blood coagulation, agglutination, fibrinolysis tests and, generally, assays for obtaining information on the clotting or lytic (lysis) process. Others assays that induce a change in the viscosity of the fluid sample, including immunoassays and affinity-based chemical or biologic assays, may also be conducted using the cartridges and methods of the present invention.

Thus, the present invention is useful for providing information concerning the discrete events that may accompany the clotting process (e.g., clot formation, clot retraction, or clot lysis), as well as provide insight into the overall event. In addition, the present invention may be useful in distinguishing between platelet-rich and platelet-poor plasma depending on the clotting profile of the sample. (See, Shenaq, S. A. and Saleem, A. in *Effective Hemostasis in Cardiac Surgery*, Ellison, N. and Jobes, D. R. (Eds.), W. B. Saunders Co. (1988) pp. 183–193.) The present invention may also provide information useful to physicians developing a prognosis for patients following cardiopulmonary bypass surgery. Post-operative bleeding is a major concern for such patients. (See, Shenaq and Saleem, Ibid. and Keeth, J. et al. *Proc. Am. Acad. Cardiovas. Perfusion* (1988) 9:22–25.)

Figure 5A:
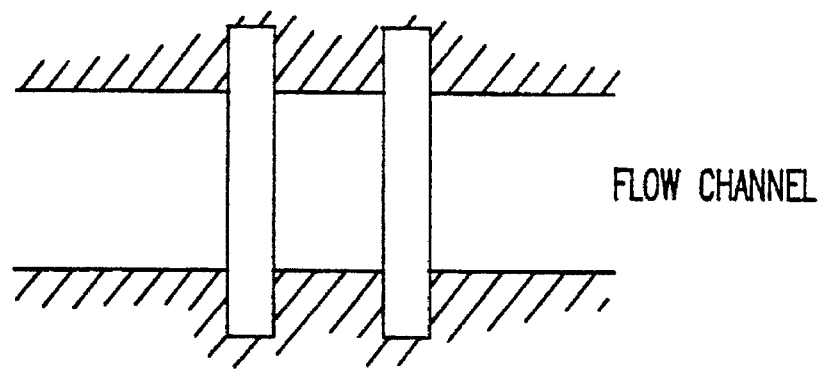
FIG. 5A shows the right angle or orthogonal configuration of a conductivity sensor of the present invention. The flow channel is indicated to the right of this particular embodiment of the invention.

In a particular embodiment of the present invention, a cartridge is provided for conducting an assay responsive to a change in the viscosity of a fluid sample. Preferably, the cartridge comprises a sensor that can detect the displacement of a fluid sample across the sensor, most preferably a conductivity sensor. A conductivity sensor suitable for use in the present invention is described, for example, in U.S. Pat. No. 5,200,051, incorporated herein by reference. Referring now to the Figures, FIG. 5A illustrates one configuration of a conductivity sensor in which the sensor electrodes are positioned orthogonal to the flow of the fluid sample. Hence, the signal output of the sensor varies as a liquid comes into or out of contact with one or both sensor electrodes since the conductivity of the liquid is different from that of air. It should be understood, however, that on retraction of the bulk sample from the sensor, a thin coat of liquid may remain on the sensor surfaces. This thin liquid coating has an impedance that is significantly lower than air. Hence, the signal output may actually reflect the difference between the conductivity of the bulk sample and this thin liquid coating. For a detailed discussion of sensor "wet-up" phenomena, the reader is referred to the disclosure of U.S. Pat. No. 5,112,455, incorporated herein by reference.

Figure 5B:
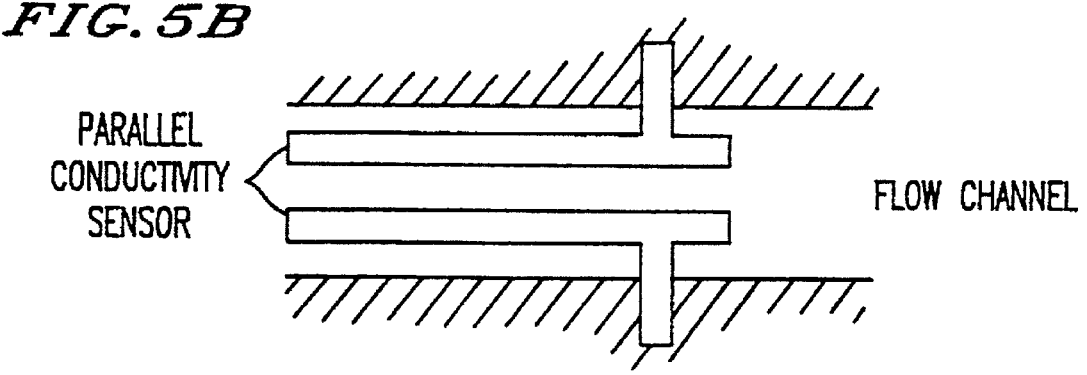
FIG. 5B is an illustration of an exemplary parallel conductivity sensor configuration of the present invention.
Figure 5C:
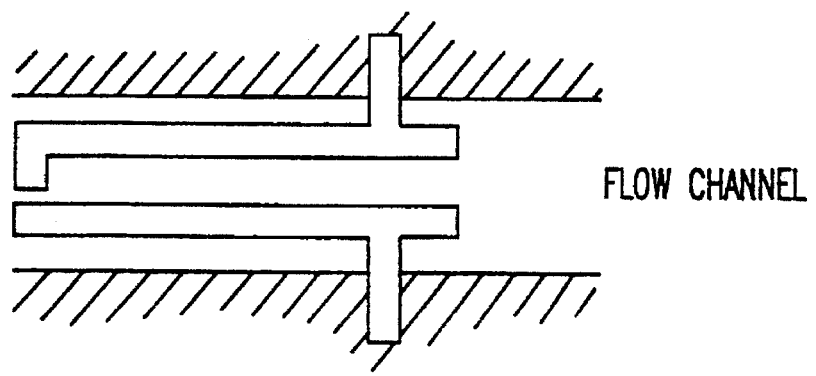
FIG. 5C illustrates one embodiment of the sensor configuration in which the electrode distance varies from the proximal end of the sensor to the distal end.

Alternatively, the sensor electrodes can be positioned longitudinally, that is, parallel to the fluid flow, as shown in FIG. 5B. In this configuration, the signal output varies as fluid covers more of (higher conductivity) or less of (lower conductivity signal output) the electrodes' surfaces. In the parallel configuration, the liquid is preferably not retracted beyond the sensor electrode altogether during the motion. FIG. 5C illustrates a further modification to the distal end of the conductivity sensor. In particular, the distance between the electrodes of the sensor can be variable. Hence, for example, the distal end can have a substantially reduced distance between the electrodes relative to the proximal end. Such a reduction gives rise to very marked changes in the signal output of the conductivity sensor thus facilitating the detection of the arrival of fluid sample at the distal end of the sensor. For the purpose of the present discussion, "proximal" means closer to the fluid source or sample retainer.

In the parallel configuration, a greater path can be provided in which the fluid sample is in contact with the sensor. It is thus possible to have a wider "triggering" window that will be able to accommodate the variability associated with the conductivity of different samples (i.e., variations in samples taken from a single patient at different times or between samples from different individuals).

Expressed differently, the signal output from an orthogonal electrode configuration tends to vary substantially in a binary fashion, reaching and declining to the extreme conductivity values rather sharply.

In contrast, the signal output of the parallel configuration is capable of exhibiting changes in conductivity in a more gradual fashion in which the value at the high conductivity end rises as the sample path length over the sensor increases. Thus, the rate of motion and position of the sample may be determined with an appropriate algorithm. This information can then be related to the actuation of the pump.

One configuration can be preferred over another depending on the circumstances. Hence, the spatial economy of the orthogonal configuration may be important in one case, whereas the greater sensitivity or versatility of the parallel arrangement may be crucial in the next case.

Figure 6:
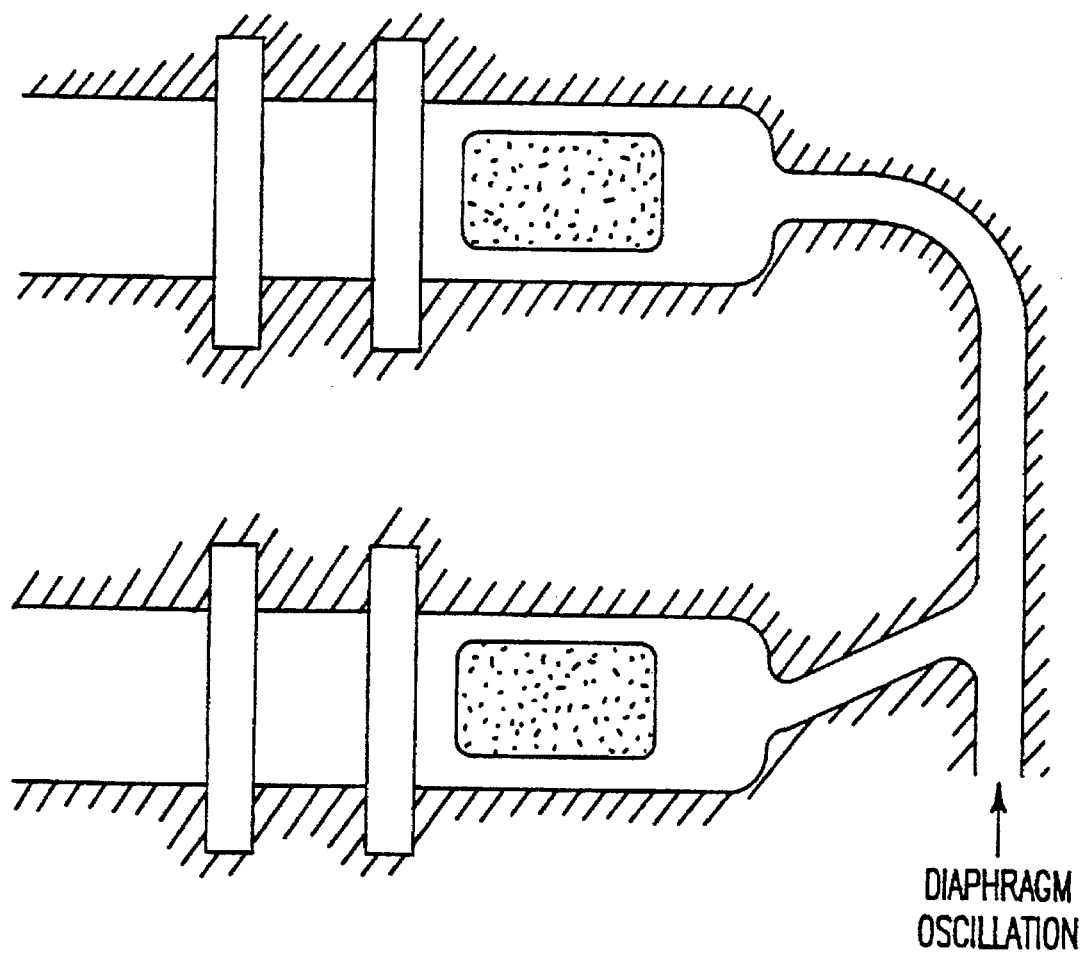
FIG. 6 illustrates one configuration of a multi-sensor, multi-reagent, and multi-flow channel embodiment of the present invention.
Figure 7:
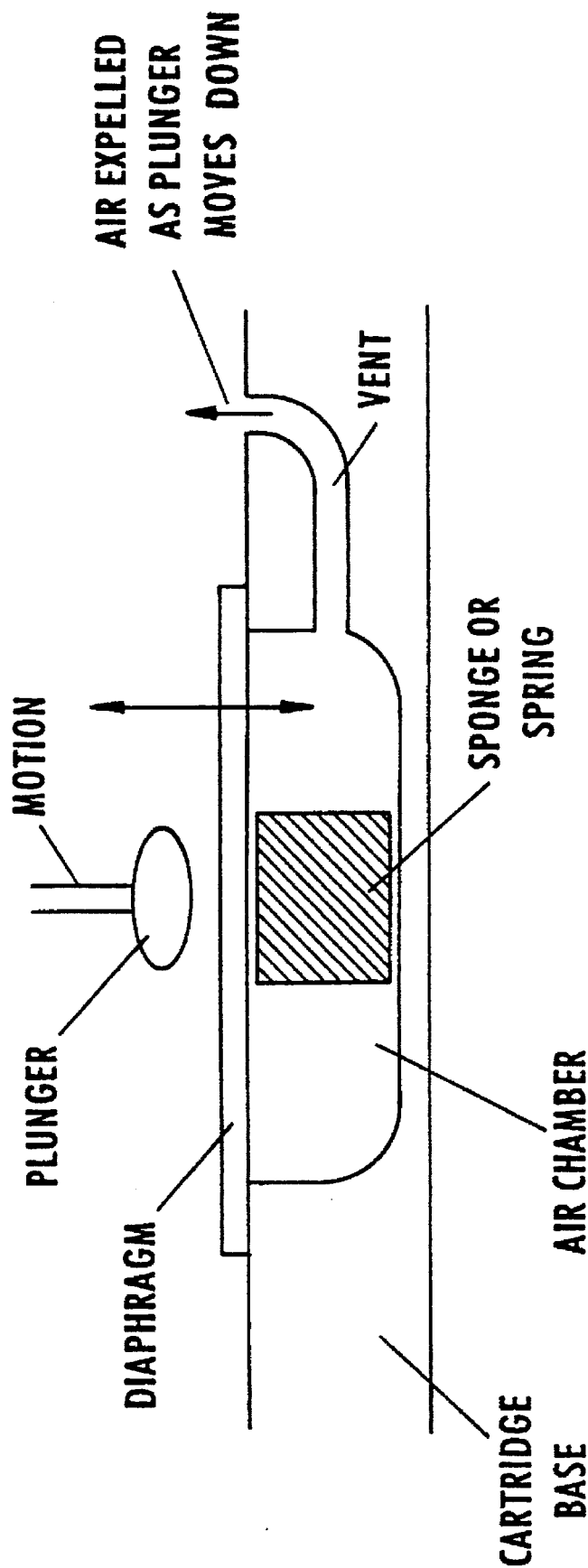
FIG. 7 illustrates a pump means according to the present invention, including a plunger and diaphragm in which the interior of the diaphragm is equipped with either a sponge or a spring.
Figure 8:
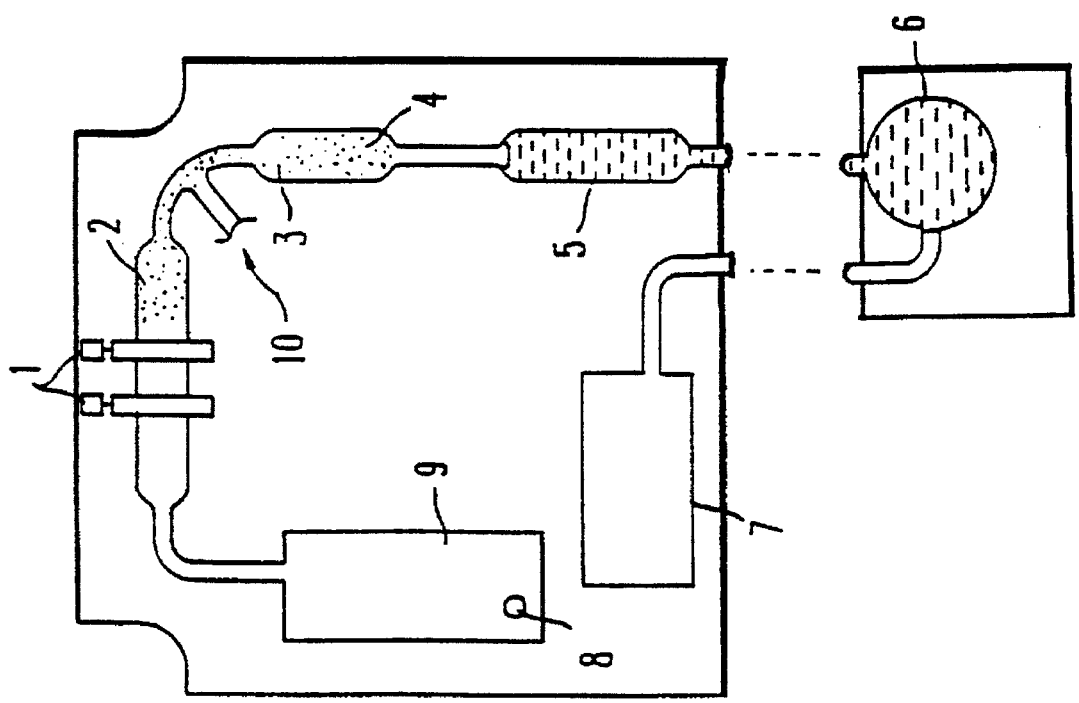
FIG. 8 is an illustration of a particular embodiment of the invention in which the sample retaining means of the claimed cartridge is in a modular form.
Figure 9A:
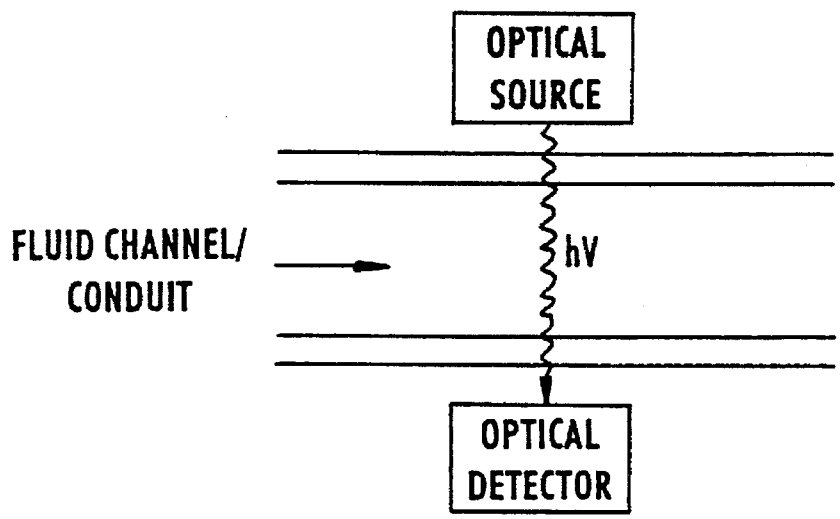
FIGS. 9A and 9B illustrate two embodiments of the invention, one relating to an optical detector and light source positioned on opposite faces of the cartridge housing (FIG. 9A) and the second having a mirrored surface such that both the light source and optical detector can be positioned on the same face of the housing.
Figure 9B:
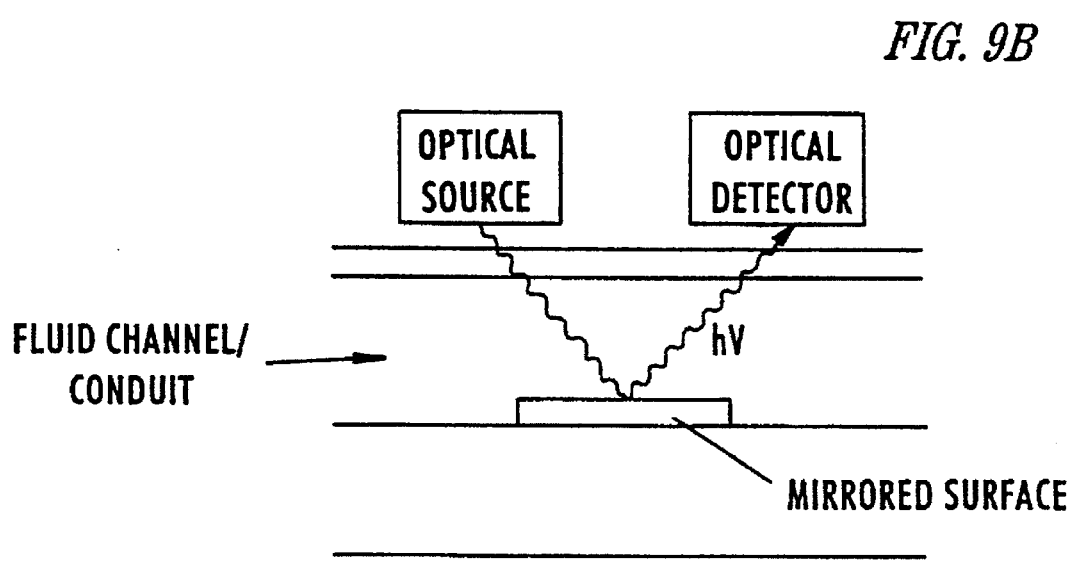

Beside the electrode configuration itself relative to the flow of the sample fluid, the dimensions and the spacings of the electrodes can also be varied according to the needs of a particular application. For example, the end distal to initial fluid contact may be modified such that the distance between electrodes is significantly reduced (See FIG. 5C). When fluid contacts this distal end of the sensor, the electrode geometry results in a significant decrease in conductivity, thus enabling a more exact determination of when the fluid sample reaches the distal end of the sensor. In addition, more complex multiple test cartridge designs can be contemplated. For instance, FIG. 6 shows multiple conduits each with sensors and different reagents, yet requiring only one diaphragm oscillation.

It should be pointed out that the portion of the sample fluid, which clots, coagulates or, otherwise, undergoes the change in viscosity, need not be in direct contact with, i.e., directly over, the sensor for the change in the viscosity of the sample fluid to be detected. All that is required is that the sample fluid be in fluid communication with the sensor. By "fluid communication" it is meant that a first component of interest, e.g., a blood sample, forms a part of a contiguous segment, some portion of which is in contact with the sensor, e.g., a conductivity electrode, such that any physical change experienced by the first component is communicable to or exerts an effect on the portion of the contiguous segment in contact with the sensor. Hence, all the parts of the contiguous segment should move in response to the compression and decompression of the diaphragm. For example, a contiguous segment may be comprised of four parts: (i) calibrant fluid, (ii) first air pocket, (iii) blood sample, and (iv) second air pocket, the second air pocket separating the blood sample from the diaphragm. Such a contiguous segment would move in its entirety in response to the variably applied pressure exerted against the diaphragm. However, "fluid communication" means, in addition, that the rate at which the entire segment oscillates is governed by the most viscous component or part of the entire segment. In the case of the segment described above, that most viscous part is most preferably the blood sample that is also undergoing a change in viscosity.

Thus, a clot may form at a point that is some distance from the sensor electrodes but, as long as some fluid is in physical contact with the sensor and is in "fluid communication" with the clotting fluid, the clot formation will nonetheless effect a change in the oscillation frequency or amplitude of the entire segment. In the example described above, the calibrant fluid may be directly over the sensor electrodes and the clotting blood may be closer to the diaphragm. Yet, information regarding the clotting phenomenon may be relayed by way of changes in the entire segment's movement, preferably, reciprocating motion, over the sensor electrodes. As noted above, the fluid directly above the sensor electrodes may even be separated from the clotting fluid by an air pocket. Because the air pocket is still a fluid material that can respond to changes in the applied pressure, the coagulating fluid or fluid undergoing the change in viscosity is still in "fluid communication" with the sensor.

In a specific embodiment of the present invention, a cartridge is contemplated which further comprises at least one conduit connecting the sample retainer to the sensor. In another embodiment, the cartridge further comprises at least two conduits connected to the sample retainer, at least one of which conduits is connected to a sensor. A preferred conduit configuration is illustrated in FIG. 6. One or more reagents capable of promoting a change in the viscosity of the fluid is positioned in one or more conduits.

The assay of the present invention is based on the ability of the sensor to detect changes in the oscillation frequency or amplitude of a sample fluid. Thus, a variety of assays may be adapted for and conducted through the present invention, including but not limited to, a fluid coagulation test, a fluid agglutination assay, immunoassays, an activated partial thromboplastin time (APTT), a prothrombin time (PT), and an activated clotting time (ACT).

Reagents for conducting the various assays mentioned above are well known in the art. For example, reagents for promoting the coagulation of blood may comprise calcium and a phospholipid or calcium and tissue thromboplastin. Activators for ACT include kaolin, diatomaceous earth, celite, finely divided glass and the like: Jacobs et al. *Laboratory Test Handbook*, Lexi-Comp Inc., Stow OH (1980) pp. 370-371.

Furthermore, the reagent may be formulated to promote its dissolution in the fluid sample. Such formulations may include simply aqueous or non-aqueous solutions of a given reagent to which various additives, such as salts, proteins, sugars or saccharides and the like may optionally be added. Certain formulations may include gelatin-containing compositions. Yet others may comprise emulsions.

In any case, the reagent compositions are preferably established on the cartridges of the present invention in a manner that enhances their dissolution upon contact with the sample fluid. High purity materials may be dispensed from a solution, for example, from which the solid reagent may crystalize on evaporation of the solvent. The resulting crystalline material may be more readily soluble in the sample fluid than a non-crystalline material. Alternatively, the reagent compositions may be established as a series or group of microdroplets. Other methods of establishing reagent layers may be used, including the methods disclosed in U.S. Pat. No. 5,200,051, the entire disclosure of which is incorporated herein by reference.

As described above, the preferred cartridge of the present invention includes a pump means for reversibly applying pressure against the sample fluid. More preferably, the pump means comprises a resilient diaphragm that is connected to the sample retainer. To assist in preserving the resiliency of the diaphragm and to promote the rapid, reproducible compression and decompression of the diaphragm, the diaphragm can be equipped with an internal spring or an internal sponge. The sponge may be made of any suitably resilient durable material, like natural or synthetic rubber and the like.

The apparatus of the present invention is preferably adapted for insertion into an external reading device that provides additional control, processing, mechanical, and reading elements. Such an external reading device may be a hand held instrument like that described in U.S. Pat. No. 5,096,669, the complete disclosure of which is incorporated herein by reference. Hence, the cartridge of the present invention is preferably equipped with a sensor that provides a signal to an external reading device which, in turn, actuates a plunger for compressing and decompressing the diaphragm. More specifically, the sensor is a conductivity sensor and the signal relates to the output of the sensor whereby an output below a first preselected value causes the reading device to actuate the plunger to compress the diaphragm and an output above a second preselected value causes the reading device to actuate the plunger to decompress the diaphragm. Of course, the first and second preselected values may be the same or they may be widely different according to the needs of the particular application. Preferably, the feedback mechanism is such that the actuating means automatically shuts down, during, for example, a coagulation test, when the sample has clotted sufficiently such that the electromotive force required to depress the plunger exceeds a certain preselected value. Of course, in the fibrinolysis test, the plunging action continues until lysis of the clotted or partially clotted sample is detected. The cartridge, moreover, can be mechanically or electronically labeled such that the external reading device can distinguish between the different tests.

In an alternative embodiment, the plunging action may be fixed at a constant rate. In this embodiment, changes in the resulting signal output may include a decrease in the amplitude of the conductivity output (e.g., in a parallel sensor configuration) or the development of a certain lag in the reciprocal motion of the sample fluid such that a change in frequency is also observed.

The external reading device may also comprise connectors for electrically contacting the sensor of the cartridge (See, for example, U.S. Pat. No. 4,954,087, incorporated herein by reference). Methods for processing the sensor output for controlling the actuation mechanisms are also contemplated by the present invention.

The present invention also contemplates a cartridge for facilitating the measurement of a change in the viscosity of a fluid sample which comprises (a) a housing capable of being charged with a fluid sample and equipped with a sample displacement means for applying a force against the fluid sample effective to displace at least a portion of the fluid sample within the housing; (b) at least one reagent, contained within the housing, capable after contact with the fluid sample of promoting a change in the viscosity of the fluid sample; and (c) at least one region, defined within the housing, in which the position of the interface of the fluid sample and air can be monitored as the interface moves with the displacement of the fluid sample.

In particular, the region within the housing may comprise a transparent window through which the position of the interface may be determined by optical detection means. Thus, the cartridge may be engaged with or placed within a detection device that comprises a light detector. The light detector may be positioned on one face of the cartridge housing. Alternatively, the optical detection means may further comprise a light source which may optionally be positioned on the face of the housing opposite the light detector. However, the cartridge housing may be modified to include a reflective material, e.g., a small mirror, which is capable of reflecting an incoming beam of light back in the general direction of the light source. Hence, in particular embodiments, the light detector may be positioned on the same side of the housing as the light source.

As noted previously, a variety of fluid samples may be assayed according to the present method. Most advantageously, however, the biological fluid can either be whole blood, heparinized blood, citrated blood or plasma. However, the cartridges of the present invention may also be exposed to other fluids, including a calibrant fluid at least a portion of which may be displaced across the sensor to calibrate the sensor output. As already mentioned above, the calibrant fluid may be displaced across the sensor in a substantially reciprocating manner while the calibrant fluid is in fluid communication with the blood or fluid sample, such that the blood or fluid sample need not be in direct contact with the sensor.

According to another aspect of the present invention, a cartridge of modular design is contemplated in which at least one element of the cartridge may be attached or detached in modular form. In particular, that element is preferably the sample retainer. Thus, the sample retainer may be used, while detached from the cartridge, to collect the sample fluid, e.g., whole blood. For instance, the sample retainer may be equipped with a capillary tube and reservoir that can be used to collect blood sample from a fingerstick or from a Vacutainer™. Alternatively, the sample retainer may include a vacuum-sealed reservoir for receiving blood from a cannula. The sample retainer is then connected to the cartridge such that the blood sample contained therein may be displaced by the sample displacement means within the housing. Once the modular sample retainer is connected to the cartridge, the external reading device may be engaged to commence the assay.

The present invention is likewise directed to a method of conducting an assay responsive to a change in the viscosity of a fluid sample comprising: (a) placing a fluid sample in a sample retainer for retaining the fluid sample out of contact with a sensor and a reagent, the sensor sensitive to the displacement of the fluid sample across the sensor and the reagent capable of promoting a change in the viscosity of the fluid sample; (b) reversibly applying pressure against the fluid sample in the sample retainer to displace at least a portion of the fluid sample across the sensor, preferably, in a substantially reciprocating manner, such that the reagent contacts and promotes the viscosity change of the fluid sample; (c) detecting the reciprocal displacement of the fluid sample across the sensor to indicate a change in the viscosity of the fluid sample. Most of the steps of the assay, preferably the sample retention and displacement steps, is carried out on a cartridge comprising a sample retainer, sensor, and pump means for reversibly applying pressure to the sample or calibrant fluid.

As discussed above for the apparatus of the present invention, the present method is compatible with a number of testing procedures that involve a change in the viscosity of the sample fluid, typically a liquid such as whole blood. Thus, the present method can be adapted for conducting assays, including but not limited to, a fluid coagulation test, a fluid agglutination assay, an immunoassay [e.g., an immunoassay that tests for the presence of small molecules, like drug substances, whether therapeutic or an abused substance, such as theophylline, digoxin, phenytoin, thyroxins, cocaine and amphetamines; biomolecules like peptides, oligopeptide, polypeptides (e.g., proteins or globulins IgA, IgG, IgM), nucleotides, oligonucleotides or polynucleotides (e.g., nucleotide analogs, specific DNA or RNA sequences, particular genes), and sugars, oligosaccharides and polysaccharides (e.g., structural components of tissues or as parts of glycoproteins)], an activated partial thromboplastin time (APTT), a prothrombin time (PT), partial thromboplastin time (PTT), thrombin clotting time (TCT) or an activated clotting time (ACT).

According to a specific embodiment of the present invention, a method is disclosed for conducting a whole blood fibrinolysis test which includes: (a) placing a whole blood sample in a sample retainer for retaining the sample out of contact with a sensor and a reagent, the sensor sensitive to the displacement of the sample across the sensor and the reagent capable of promoting the coagulation of the sample; (b) reversibly applying pressure against the sample in the sample retainer to displace at least a portion of the sample across the sensor, preferably, in a substantially reciprocating manner, such that the reagent contacts and promotes the coagulation or partial coagulation of the sample; (c) maintaining the reversibly applied pressure against the coagulated or partially coagulated sample until fibrinolytic processes cause the coagulated or partially coagulated sample to become less viscous, allowing increased displacement of at least a portion of the lysed sample across the sensor in a substantially reciprocating manner.

In the fibrinolysis test of the present invention, the sample fluid may be treated with a second reagent capable of promoting the fibrinolysis of the sample when the sample is coagulated or partially coagulated. The sample fluid may be exposed to the fibrinolysis promoting agent practically at any time before or after the sample fluid comes into contact with the reagent that promotes the coagulation or clotting of the sample fluid, typically, whole blood. A number of fibrinolysis promoting agents can be used, including tissue plasminogen activator (tPA), streptokinase, urokinase, and the like.

The present invention may also then be adapted to a method of selecting a fibrinolysis promoting agent useful in the treatment of a particular subject. Because individuals may respond differently to treatment using one or more fibrinolysis promoting agents, it would be extremely useful to have an assay that may predict which member of a given set of fibrinolysis promoting agents a particular individual may best respond to. Hence, according to the present invention, a method is disclosed which includes the steps of: (a) conducting a fibrinolysis test on a sample of whole blood obtained from a subject, the test comprising, (i) placing the sample in a sample retainer for retaining the sample out of contact with a sensor and a reagent, the sensor sensitive to the displacement of the sample across the sensor and the reagent capable of promoting the coagulation of the sample, (ii) reversibly applying pressure against the sample in the sample retainer to displace at least a portion of the sample across the sensor, preferably, in a substantially reciprocating manner, such that the reagent contacts and promotes the coagulation or partial coagulation of the sample, (iii) treating the sample at any time before or after the sample contacts the reagent with a fibrinolysis promoting agent, and (iv) maintaining the reversibly applied pressure against the coagulated or partially coagulated sample until natural fibrinolytic processes cause the coagulated or partially coagulated sample to become less viscous, allowing increased displacement of at least a portion of the lysed sample across the sensor in a substantially reciprocating manner; (b) repeating the fibrinolysis test of step (a) one or more times using one or more different fibrinolysis promoting agents; (c) comparing the results of the tests to determine the most efficacious fibrinolysis promoting agent for the subject.

It should be noted that the present apparatus and methods are most preferably stored or, during test conditions, maintained at an optimum temperature. For example, certain reagents may be temperature sensitive, e.g., the PT reagent. Thus, to improve the shelf life of a cartridge, which includes temperature sensitive reagents, the apparatus is preferably stored desiccated at 4° C. Moreover, certain reagent formulations may prove beneficial, such as mixing the reagent in a stabilizing, easily dissolvable gelatin matrix. During the test itself, the cartridge may also be maintained, for example, at physiologic temperature, preferably at 37° C.±0.1° C.

The present invention is illustrated further by the following specific examples, the detailed description of which should not be construed to limit the invention in any particular manner.

EXAMPLES

PT Test Cartridge

A cartridge suitable for performing a PT test using a conductimetric sensor is described below.

Figure 1A:
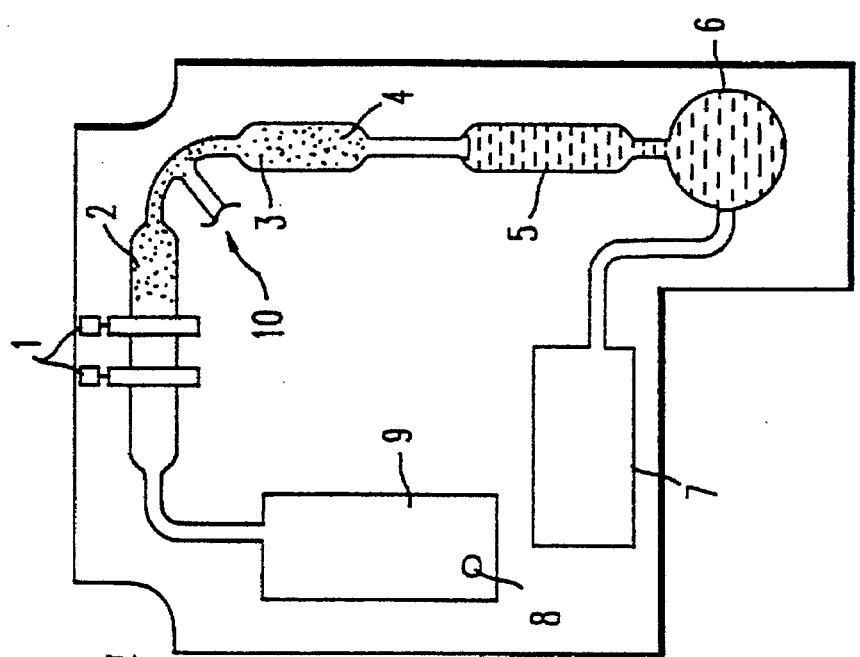
FIG. 1A is an illustration of a particular embodiment of the cartridge of the present invention. In particular, 1 represents the conductivity sensor in an orthogonal configuration. The sample flow channel is marked by 2, and the reagent chamber is indicated by 3. Alternatively, the reagent can be in the sensor area of 1. An air segment 4 may also be present in the reagent chamber. The point 5 marks the sample holding chamber and 6 indicates a sealable sample port. The diaphragm, which applies pressure to move the sample through the flow channels, is indicated by 7. The waste chamber is 9 and 8 indicates a vent in the waste chamber.
Figure 1B:
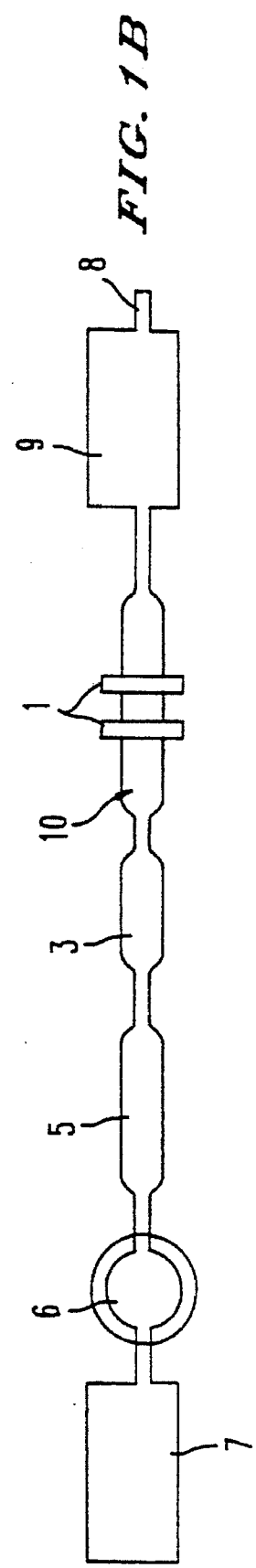
FIG. 1B is a topological rendition of the cartridge of FIG. 1A. Calibrant fluid can be introduced at 10, also illustrated in FIG. 1A, above.

Sigma PT reagents comprising thromboplastin and calcium are dissolved in distilled deionized water and then manually dispensed by means of a syringe into the flow channel and air segment regions of cartridge covers, but not into the blood holding chamber, as illustrated in FIG. 1A. After the reagent has dried, cartridge covers are assembled with the cartridge bases. FIG. 1B is a topological rendition of the diagram illustrated in FIG. 1A.

Figure 2A:
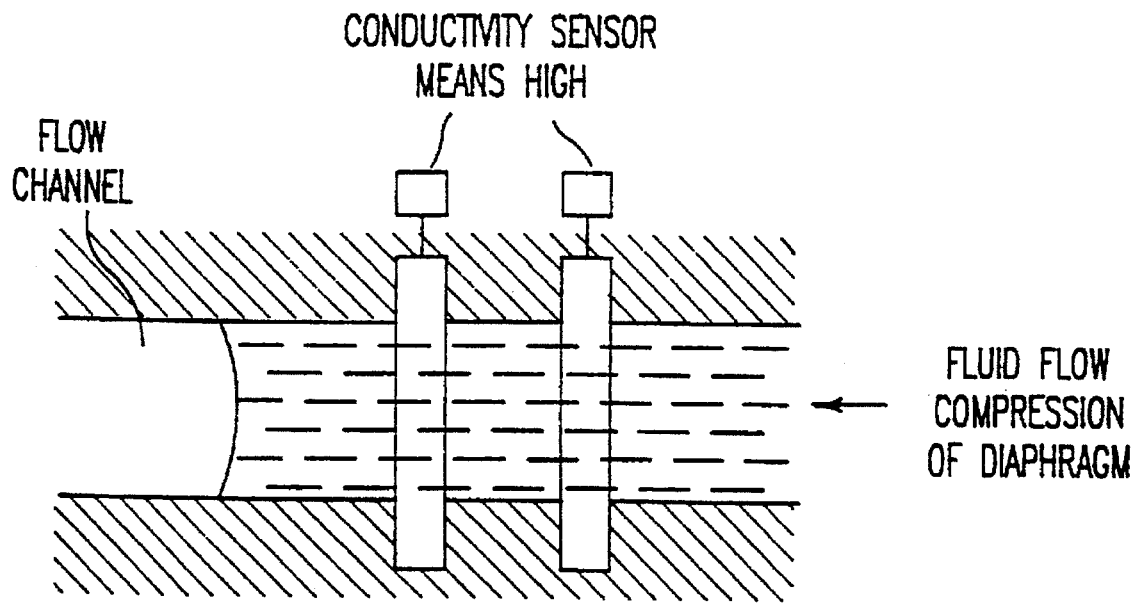
FIGS. 2A and 2B illustrate a sequence of events in which (a) marks the compression of the diaphragm, resulting in the flow of the fluid sample over the conductivity sensors (the sensor measures high conductivity), (b) marks the decompression of the diaphragm and the resulting retraction of the fluid sample (the sensor measures low conductivity), and (c) the cycle of fluid sample movement is repeated to oscillate the sample over the sensor.
Figure 2B:
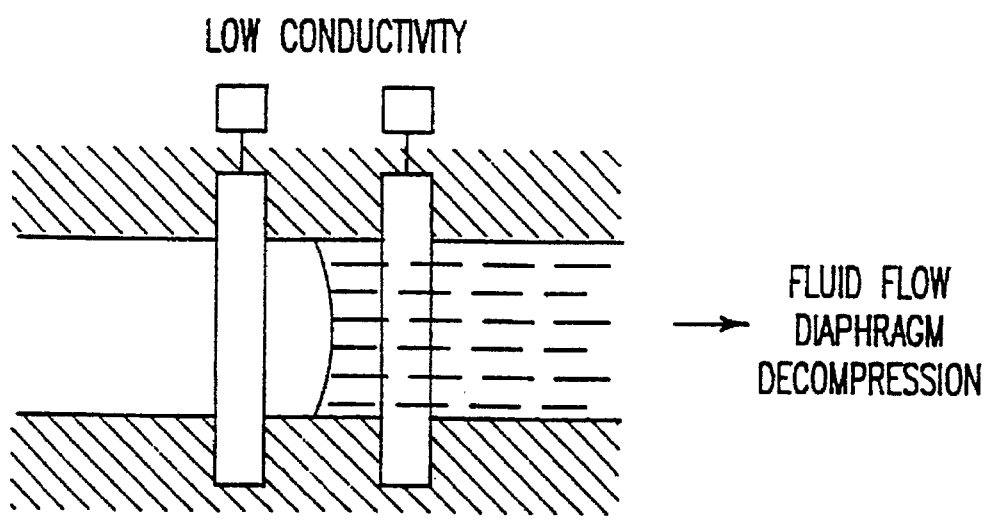

Next, citrated whole-blood is introduced into the blood holding chamber (i.e., out of contact with the reagents) and then manually advanced and oscillated over the sensor region by repeatedly pressing on the diaphragm, as shown in FIG. 2. At first, as revealed by visual inspection, the blood moves easily as it dissolves and mixes with the reagents. However, a brief period after first contacting the reagents, the blood clots. Further pressure applied to the diaphragm fails to move the blood in the sensor region because of the dramatic change in the viscosity of the whole blood sample. Several cartridges are tested similarly and all provided results similar to that presented above.

Clot formation is detected more effectively by including a conductivity sensor and operating the cartridge in conjunction with the analyzer. Iridium electrodes are selected for the sensor, although other noble metals, such as gold or platinum, may also be used. Silver may also have some utility as the electrode material. The blood is oscillated over the conductivity sensor by using the output of the conductivity sensor to control the compression and decompression of the diaphragm by the plunger element of the analyzer (i.e., the external reading device). Once blood covers both conductivity electrodes, the lower measured impedance triggers retraction of the plunger, decompressing the diaphragm. When the blood moves back or retracts off the electrodes, the higher measured impedance triggers downward motion of the plunger and compression of the diaphragm. In this way, blood is moved in a substantially reciprocating manner over the conductivity sensor.

The diaphragm may also be compressed and decompressed at a constant rate as described previously.

Figure 3A:
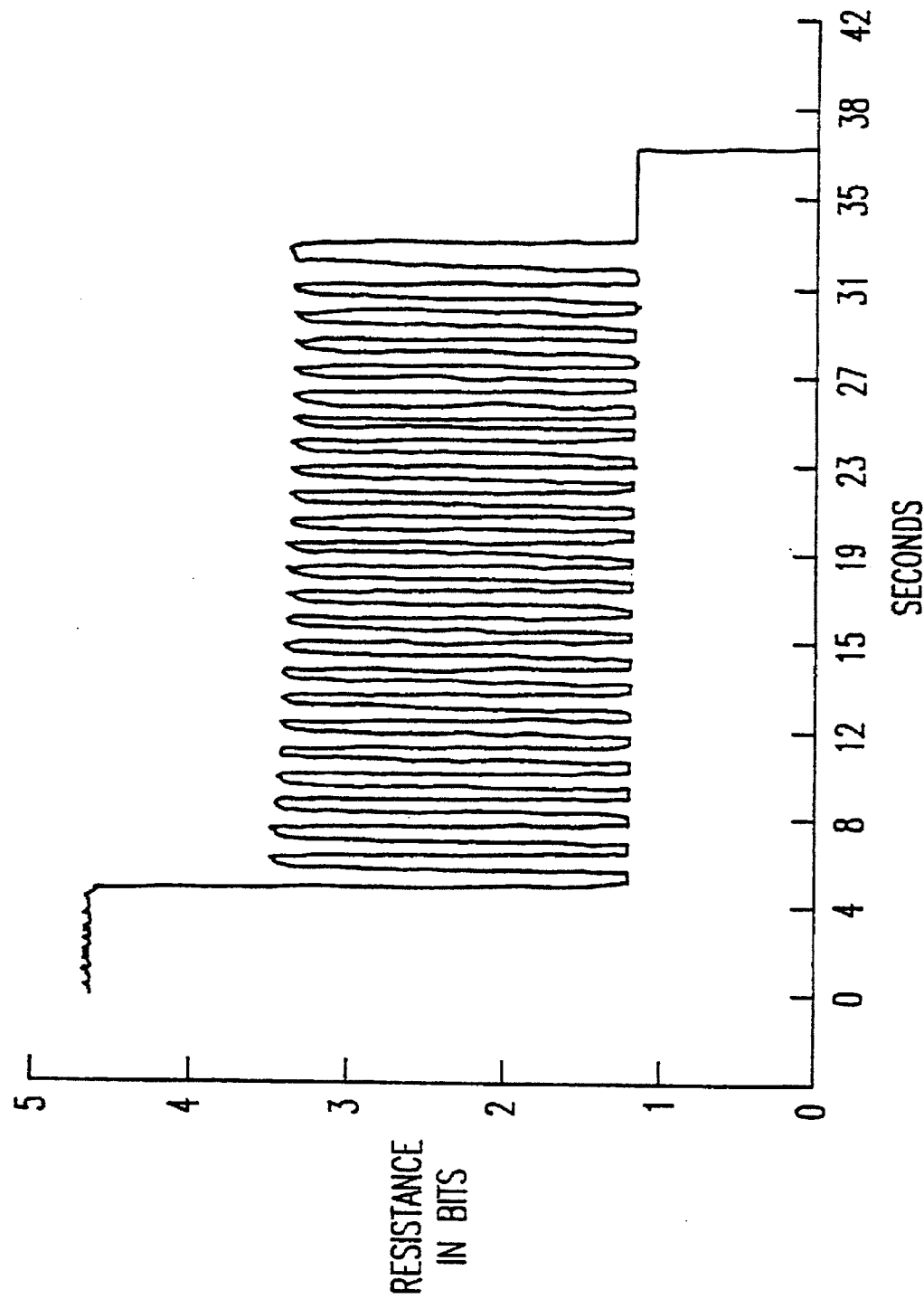
FIG. 3A illustrates a typical orthogonal sensor output when reagents are present to cause the clotting of a blood sample.
Figure 3B:
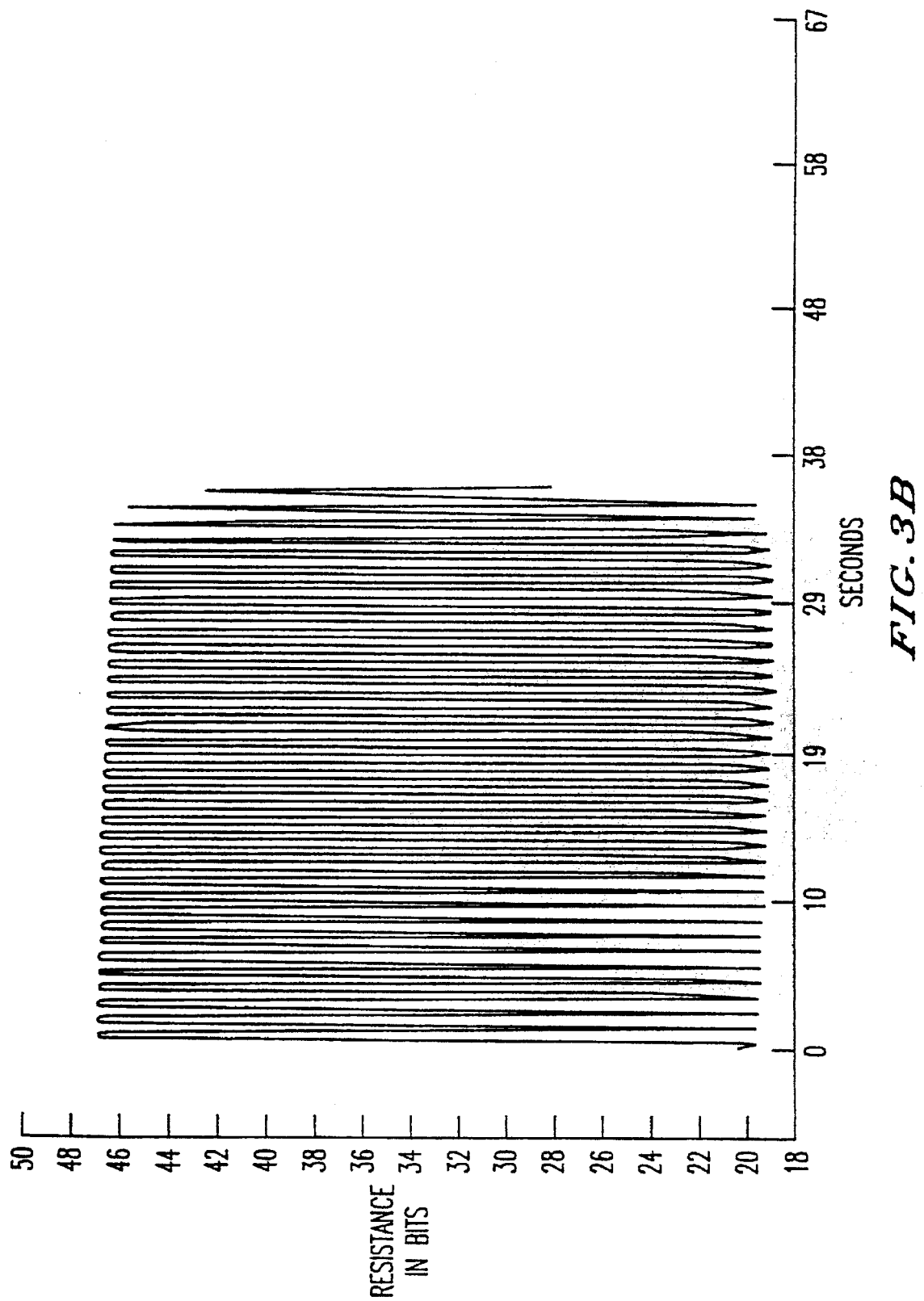
FIG. 3B illustrates a typical parallel conductivity sensor output in the presence of clotting reagents.
Figure 4A:
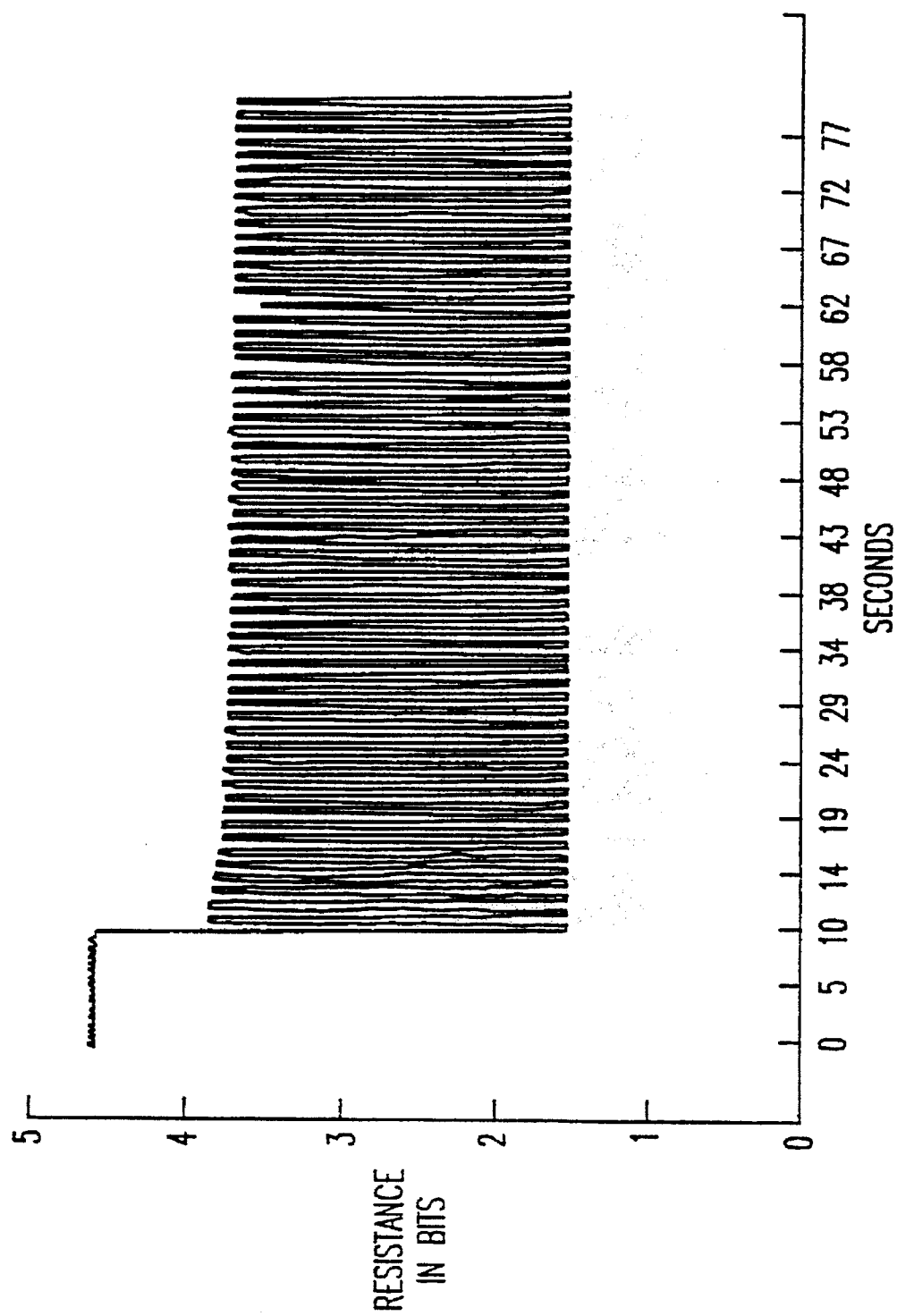
FIGS. 4A and 4B show representative signal outputs from the orthogonal conductivity sensor and parallel conductivity sensor, respectively, in the absence of procoagulation reagents.
Figure 4B:
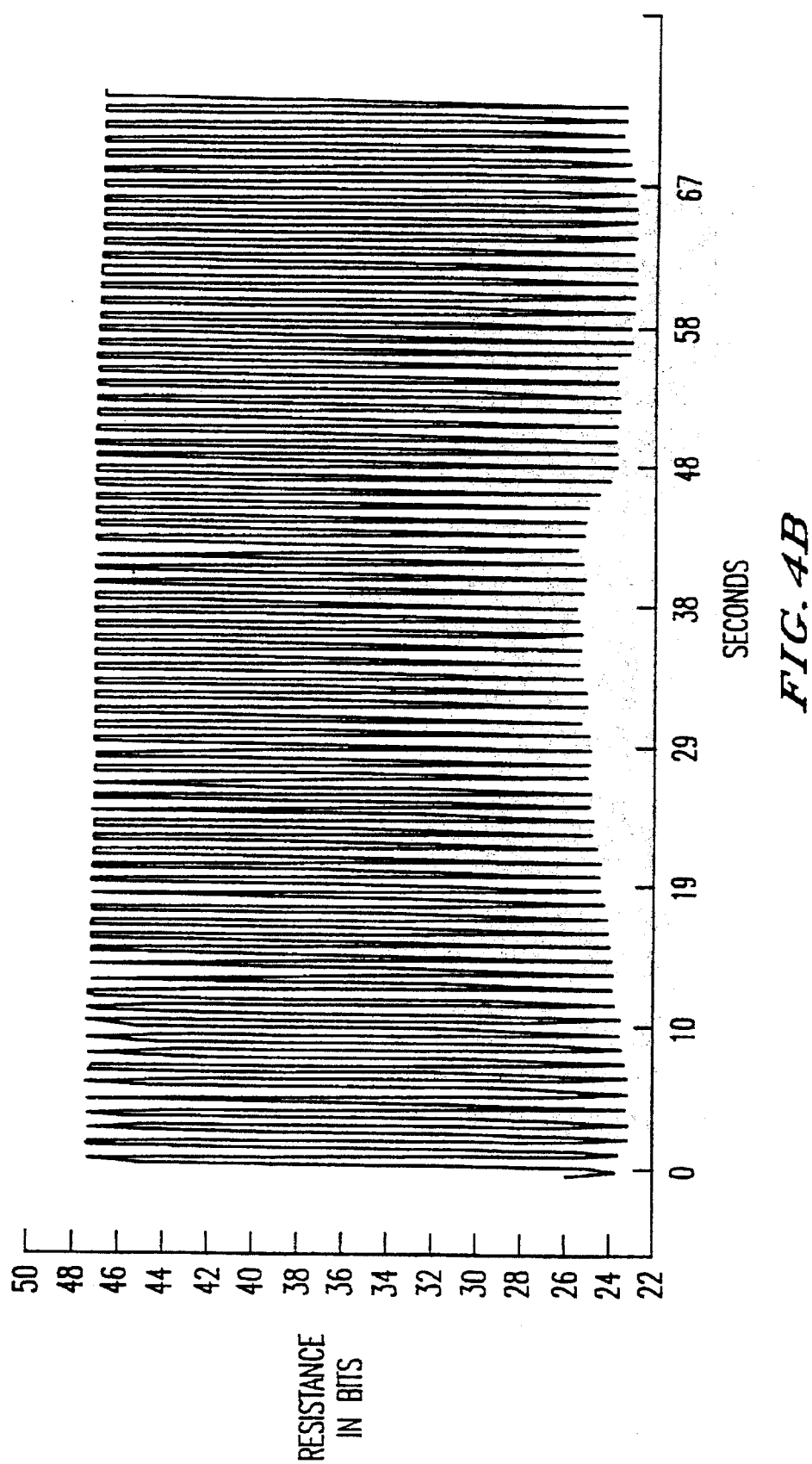

Several cartridges prepared in the manner described above are tested with the analyzer and the output of the conductivity sensor recorded. FIGS. 3A (orthogonal configuration) and 3B (parallel configuration) show typical outputs when reagents that promote coagulation are present. FIGS. 4A (orthogonal) and 4B (parallel) show typical outputs of control runs in which the sample fluids are not exposed to reagents that promote coagulation.

These and other experiments directed to other assay methods, such as APTT, ACT, PTT, TCT and fibrinolysis, demonstrate the essential features of the invention in which a conductivity sensor can be used to monitor motion, cessation of or changes in the frequency, phase of oscillation or amplitude of motion of a blood sample, thus distinguishing unclotted (or lysed blood) from clotted blood. By "phase of oscillation" is meant differences in phase between actuation of the plunger and the resultant position of the fluid sample over the sensor. Furthermore, these examples also show that a signal output feedback method allows the detection of subtle changes in the viscosity of the sample fluid prior to actual clot formation. The cartridge comprising the pump means in the form of a resilient diaphragm is demonstrated to provide a controlled oscillation of a whole blood sample over a conductivity sensor, and the required reagents, whether coagulation promoters or fibrinolysis promoters, are shown to retain activity after being established on the cartridge. These reagents subsequently dissolve and mix with the whole blood sample in a controlled manner.

Microfabricated Single-Use Cartridge For Blood Coagulation/Fibrinolysis Testing

The i-STAT 6+ cartridge, available from i-STAT Corporation, Princeton, N.J. 08540, is modified to include a conductimetric sensor in a parallel orientation and reagents for promoting the coagulation of whole blood. The reagents are established conveniently in a conduit connecting the sample retainer and the conductivity sensor.

Additionally, fibrinolysis promoting agents are also established in the conduit for those cartridges to be used for fibrinolysis testing.

A resilient diaphragm is used as the bladder portion of the cartridge and an internal rubbery sponge is optionally inserted in the diaphragm.

Additional modifications to this cartridge include multiple conduits, additional conductivity sensors, and different coagulation and/or fibrinolysis promoting reagents. For details of the microfabrication of sensing devices, the reader is referred to the disclosure of U.S. Pat. No. 5,200,051, incorporated herein by reference.

The foregoing specific examples illustrate the working elements of the present invention. Other embodiments of the present invention not specifically described are apparent to those of ordinary skill in the art but are understood to fall within the scope and spirit of the invention. The foregoing specific examples are not to construed as limiting the invention in any manner, which invention is limited solely by the following claims.

What is claimed is:

1. A cartridge for measuring a change in the viscosity of a fluid sample comprising:

(a) a housing capable of being charged with a fluid sample and equipped with a sample displacement means for applying a force against said fluid sample effective to displace at least a portion of said fluid sample within said housing;

(b) at least one reagent, contained within said housing, capable after contact with said fluid sample of promoting a change in the viscosity of said fluid sample;

(c) at least one sensing means, contained within said housing, capable of detecting the displacement of said fluid sample.

2. The cartridge of claim 1 in which said housing is equipped with one or more connecting means for engaging said housing with one or more mechanical, electronic or optical devices.

3. The cartridge of claim 2 in which one said device comprises an external reading device.

4. The cartridge of claim 2 in which one said device comprises a sample retaining means capable of charging said housing with said fluid sample.

5. The cartridge of claim 4 in which said sample retaining means includes a fluid sampling means.

6. The cartridge of claim 1 which further comprises a sample retaining means that forms an integral part of said housing.

7. The cartridge of claim 6 in which said sample retaining means retains said fluid sample out of contact with said sensing means and said reagent.

8. The cartridge of claim 1 in which said sample displacement means comprises a pump means that forms an integral part of said housing.

9. The cartridge of claim 1 or 8 in which said sample displacement means is capable of applying said force against said fluid sample such that at least a portion of said fluid sample is displaced across said sensing means.

10. The cartridge of claim 9 in which said force is reversible, such that at least a portion of said fluid sample is displaced back and forth across said sensing means in a substantially reciprocating manner.

11. The cartridge of claim 1 or 8 in which said displacement causes said fluid sample to come in contact with said reagent.

12. The cartridge of claim 1 in which said sensing means is capable of detecting electrical changes in a fluid.

13. The cartridge of claim 1 in which said sensing means is capable of detecting the position of the interface between a gas and a liquid.

14. The cartridge of claim 13 in which said liquid is said fluid sample or a calibrant.

15. The cartridge of claim 12 in which said sensing means comprises a conductivity sensor.

16. The cartridge of claim 12, 13 or 15 in which said sensing means is microfabricated.

17. The cartridge of claim 16 in which said sensing means comprises a conductivity sensor.

18. The cartridge of claim 17 in which said sensor comprises a pair of metal electrodes.

19. The cartridge of claim 18 in which said metal is a noble metal selected from the group consisting of gold, platinum, and iridium.

20. The cartridge of claim 18 in which said pair of electrodes is arranged in a configuration that is substantially parallel to the fluid sample flow.

21. The cartridge of claim 18 in which said pair of electrodes is arranged in a configuration that is substantially orthogonal to the fluid sample flow.

22. The cartridge of claim 18 having a variable distance between said electrodes of said pair.

23. The cartridge of claim 22 in which the distance between said pair of electrodes at the distal end of said sensor is substantially reduced relative to the distance at the proximal end of said sensor.

24. The cartridge of claim 1 in which said reagent is for an assay selected from the group consisting of prothrombin time (PT), partial thromboplastin time (PTT), activated partial thromboplastin time (APTT), thrombin clotting time (TCT), activated clotting time (ACT), and fibrinogen assay.

25. A cartridge for measuring a change in the viscosity of a fluid sample comprising:

(a) a housing capable of being charged with a fluid sample and equipped with a pump means capable of applying a force against said fluid sample effective to displace said fluid sample within said housing;

(b) at least one reagent, contained within said housing, capable after contact with said fluid sample of promoting a change in the viscosity of said fluid sample;

(c) at least one sensing means, contained within said housing, capable of detecting the displacement of said fluid sample.

26. A cartridge for measuring a change in the viscosity of a fluid sample comprising:

(a) a housing equipped with (i) sample retaining means capable of being charged with a fluid sample, and (ii) pump means capable of applying a force against said fluid sample contained in said sample retaining means effective to displace at least a portion of said fluid sample within said housing;

(b) at least one reagent, contained within said housing, capable after contact with said fluid sample of promoting a change in the viscosity of said fluid sample;

(c) at least one sensing means, contained within said housing, capable of detecting the displacement of said fluid sample.

27. The cartridge of claim 25 or 26 which further comprises at least one conduit connecting said fluid sample to said sensing means.

28. The cartridge of claim 27 in which said reagent is located in said conduit.

29. The cartridge of claim 27 in which at least two conduits are connected to said fluid sample, at least one of which conduits is connected to said sensing means.

30. The cartridge of claim 29 in which the same reagent is located in each conduit.

31. The cartridge of claim 29 in which a different reagent is located in each conduit.

32. The cartridge of claim 25 or 26 in which said sensing means comprises a conductivity sensor.

33. The cartridge of claim 25 or 26 in which said sensing means is capable of sensing the fluid sample oscillation frequency, amplitude or changes therein.

34. The cartridge of claim 26 in which said reagent includes a reagent for a fluid coagulation test.

35. The cartridge of claim 26 in which said reagent includes a reagent for a fluid agglutination assay.

36. The cartridge of claim 26 in which said reagent includes a reagent for an immunoassay.

37. The cartridge of claim 26 in which said reagent includes a reagent for an activated partial thromboplastin time (APTT).

38. The cartridge of claim 26 in said reagent includes a reagent for a prothrombin time (PT).

39. The cartridge of claim 26 in which said reagent includes a reagent for an activated clotting time (ACT).

40. The cartridge of claim 37 in which said reagent comprises calcium and a phospholipid.

41. The cartridge of claim 38 in which said reagent comprises calcium and tissue thromboplastin.

42. The cartridge of claim 39 in which said reagent comprises a particulate material selected from the group consisting of kaolin, diatomaceous earth, celite, finely divided glass or mixtures thereof.

43. The cartridge of claim 26 in which said reagent is formulated to promote its dissolution in said fluid sample.

44. The cartridge of claim 43 in which said formulation includes an additive that promotes the dissolution of said reagent in said fluid sample.

45. The cartridge of claim 44 in which said additive is selected from the group consisting of salts, gelatins, and saccharides.

46. The cartridge of claim 26 in which said reagent is established into said housing in a manner that promotes the dissolution of said reagent in said fluid sample.

47. The cartridge of claim 46 in which said reagent is established as microdroplets from a microsyringe.

48. The cartridge of claim 25 or 26 in which said pump means comprises a resilient diaphragm in fluid communication with said sample retaining means.

49. The cartridge of claim 48 in which said diaphragm is equipped with an internal spring to promote the rapid, reproducible compression and decompression of said diaphragm.

50. The cartridge of claim 48 in which said diaphragm is equipped with an internal sponge to promote the rapid, reproducible compression and decompression of said diaphragm.

51. The cartridge of claim 25 or 26 in which said sensing means provides a signal to an external reading device that actuates a plunger for compressing and decompressing said diaphragm.

52. The cartridge of claim 51 in which said sensing means is a conductivity sensor and said signal relates to the conductivity output of said sensor whereby an output below a first preselected conductivity value causes said reading device to actuate said plunger to compress said diaphragm and an output above a second preselected conductivity value causes said reading device to actuate said plunger to decompress said diaphragm.

53. The cartridge of claim 52 in which said first and second preselected values are the same.

54. A cartridge for conducting a blood test comprising:
 (a) a housing equipped with (i) sample retaining means capable of being charged with a blood sample, and (ii) pump means capable of applying a force against said blood sample contained in said sample retaining means effective to displace at least a portion of said blood sample within said housing;
 (b) at least one reagent, contained within said housing, capable after contact with said blood sample of promoting a change in the viscosity of said blood sample;
 (c) at least one sensing means comprising a conductivity sensor, contained within said housing, capable of detecting the displacement of said blood sample, said pump means capable of reversibly applying said force such that at least a portion of said blood sample is displaced back and forth across said sensor in a substantially reciprocating manner.

55. The cartridge of claim 54 in which said test provides a prothrombin time and said reagent is a mixture comprising thromboplastin and calcium ions.

56. The cartridge of claim 54 in which said test provides an activated partial thromboplastin time and said reagent is a mixture comprising phospholipid and calcium ions.

57. The cartridge of claim 54 in which said test comprises a fibrinolysis test land said reagent is capable of promoting the coagulation or partial coagulation of said blood sample.

58. The cartridge of claim 57 in which said pump means is capable of maintaining said reversibly applied force against said coagulated or partially coagulated blood sample until fibrinolytic processes cause said coagulated or partially coagulated blood sample to become less viscous, allowing increased displacement of at least a portion of said lysed blood sample across said sensor.

59. The cartridge of claim 1, 25, 26, or 54 which further comprises a calibrant fluid, contained in said housing, at least a portion of which may be displaced across said sensor to calibrate same.

60. The cartridge of claim 59 in which said calibrant fluid is in fluid communication with said fluid or blood sample, such that the displacement of said fluid or blood sample results in the displacement of at least a portion of said calibrant fluid across said sensor.

61. The cartridge of claim 60 in which at least a portion of said calibrant fluid is displaced back and forth across said sensor in a substantially reciprocating manner.

62. The cartridge of claim 1, 25, 26 or 54 in which at least one element of said cartridge may be attached or detached in modular form.

63. The cartridge of claim 26 or 54 in which said sample retaining means may be attached or detached in modular form.

64. The cartridge of claim 63 in which said sample retaining means may be used, detached from said cartridge, to collect said fluid or blood sample.

65. A cartridge for facilitating the measurement of a change in the viscosity of a fluid sample comprising:
 (a) a housing capable of being charged with a fluid sample and equipped with a sample displacement means for applying a force against said fluid sample effective to displace at least a portion of said fluid sample within said housing;
 (b) at least one reagent, contained within said housing, capable after contact with said fluid sample of promoting a change in the viscosity of said fluid sample;
 (c) at least one region, defined within said housing, in which the position of the interface of said fluid sample and air can be monitored as said interface moves with the displacement of said fluid sample.

66. The cartridge of claim 65 in which said region comprises a transparent window through which the position of said interface may be determined by optical detection means.

67. The cartridge of claim 66 in which said optical detection means comprises a light detector positioned on one face of said housing.

68. The cartridge of claim 67 in which said optical detection means further comprises a light source positioned on the face of said housing opposite said light detector.

69. The cartridge of claim 66 in which said transparent window is equipped with a reflective material that allows the position of said interface to be determined by an optical detection means comprising a light detector and a light source positioned on the same face of said housing.

70. The cartridge of claim 69 in which said reflective material comprises a mirror.

* * * * *